an image

(12) United States Patent
Wang et al.

(10) Patent No.: US 11,162,212 B2
(45) Date of Patent: Nov. 2, 2021

(54) MELANIN-BASED CHEMICAL PROTECTIVE MATERIALS

(71) Applicant: The Government of the United States of America, as represented by the Secretary of the Navy, Arlington, VA (US)

(72) Inventors: Zheng Wang, Burke, VA (US); Brandy J. White, Washington, DC (US); Gaurav J. Vora, Washington, DC (US); Martin H. Moore, Woodbridge, VA (US)

(73) Assignee: The Government of the United States of America, as represented by the Secretary of the Navy, Washington, DC (US)

( * ) Notice: Subject to any disclaimer, the term of this patent is extended or adjusted under 35 U.S.C. 154(b) by 357 days.

(21) Appl. No.: 16/445,842

(22) Filed: Jun. 19, 2019

(65) Prior Publication Data

US 2020/0024797 A1    Jan. 23, 2020

Related U.S. Application Data

(60) Provisional application No. 62/687,580, filed on Jun. 20, 2018.

(51) Int. Cl.
| | | |
|---|---|---|
| *D06M 13/352* | (2006.01) |
| *D06M 10/08* | (2006.01) |
| *D06M 10/00* | (2006.01) |
| *C12P 17/10* | (2006.01) |
| *D06M 13/52* | (2006.01) |
| *D06M 13/513* | (2006.01) |
| *D06P 1/00* | (2006.01) |
| *D06P 5/00* | (2006.01) |
| *D06P 1/44* | (2006.01) |
| *D06P 5/20* | (2006.01) |
| *D06P 1/34* | (2006.01) |
| *D06P 5/22* | (2006.01) |

(52) U.S. Cl.
CPC ........... *D06M 13/352* (2013.01); *C12P 17/10* (2013.01); *D06M 10/003* (2013.01); *D06M 10/08* (2013.01); *D06M 13/513* (2013.01); *D06M 13/52* (2013.01); *D06P 1/0052* (2013.01); *D06M 2400/01* (2013.01); *D06P 1/34* (2013.01); *D06P 1/44* (2013.01); *D06P 5/002* (2013.01); *D06P 5/2072* (2013.01); *D06P 5/2083* (2013.01); *D06P 5/22* (2013.01)

(58) Field of Classification Search
CPC .. D06M 13/352; D06M 10/003; D06M 10/08; D06M 13/513; D06M 13/52; D06M 2400/01; C12P 17/10; D06P 1/0052; D06P 1/34; D06P 1/44; D06P 5/002; D06P 5/2072; D06P 5/2083; D06P 5/22
See application file for complete search history.

(56) References Cited

U.S. PATENT DOCUMENTS

| | | |
|---|---|---|
| 5,112,883 A | 5/1992 | Gallas |
| 9,689,111 B2 | 6/2017 | White et al. |
| 2009/0317616 A1 | 12/2009 | Kawai |
| 2014/0273688 A1* | 9/2014 | White .................. D06M 10/08 442/122 |
| 2016/0312400 A1* | 10/2016 | Casanova Royo .. D06N 3/0061 |

FOREIGN PATENT DOCUMENTS

| | | | |
|---|---|---|---|
| CN | 106833310 A | 6/2017 | |
| CN | 106958151 * | 7/2017 | ............... D06P 1/34 |
| KR | 10-1804910 B1 | 1/2018 | |

OTHER PUBLICATIONS

Kim, Y. J., Khetan, A., Wu, W., Chun, S. E., Viswanathan, V., Whitacre, J. F., and Bettinger, C. J. (2016) Evidence of Porphyrin-Like Structures in Natural Melanin Pigments Using Electrochemical Fingerprinting. Adv Mater 28, 3173-3180.
Schweitzer, A. D., Howell, R. C., Jiang, Z., Bryan, R. A., Gerfen, G., Chen, C. C., Mah, D., Cahill, S., Casadevall, A., and Dadachova, E. (2009) Physico-chemical evaluation of rationally designed melanins as novel nature-inspired radioprotectors. PLoS One 4, e7229.
International Search and Opinion dated Oct. 11, 2019 in PCT/US2019/037943.
"Green Synthesis of Protein Stabilized Silver Nanoparticles Using Pseudomonas fluorescens, a Marine Bacterium, and Its Biomedical Applications When Coated on Polycaprolactam" Veluchamy Prabhawathi, Ponnurengam Malliappan Sivakumar, and Mukesh Doble Industrial & Engineering Chemistry Research 2012 51 (14), 5230-5239.

* cited by examiner

*Primary Examiner* — Amina S Khan
(74) *Attorney, Agent, or Firm* — US Naval Research Laboratory; Roy Roberts

(57) ABSTRACT

The application of melanin to fabric improves resistance to chemical pass-through, with possible application in protective garments, shelters, and filtration materials.

10 Claims, 10 Drawing Sheets

MELANIN-BASED CHEMICAL PROTECTIVE MATERIALS

CROSS-REFERENCE TO RELATED APPLICATIONS

This application claims the benefit of U.S. Provisional Application No. 62/687,580 filed on Jun. 20, 2019, the entirety of which is incorporated herein by reference.

FEDERALLY-SPONSORED RESEARCH AND DEVELOPMENT

The United States Government has ownership rights in this invention. Licensing inquiries may be directed to Office of Technology Transfer, US Naval Research Laboratory, Code 1004, Washington, D.C. 20375, USA; +1.202.767.7230; techtran@nrl.navy.mil, referencing NC 108,603.

BACKGROUND

Melanins are macromolecules formed by oxidative polymerization of phenolic and/or indolic compound. These pigments, with black or brown color, are hydrophobic and negatively charged. They are ubiquitous in nature and exhibit a large variety of biological functions including structural coloration, free radical scavenging, immune response, neuroprotection, and even as photosynthetic pigments to capture ionizing radiation. In addition, this biopolymer has unique physical and chemical properties such as redox activity, semiconductor, photoconductivity, cation chelation and self-assembling into various morphologies (ref. 1). In nature, different types of melanins have been produced from various organisms and their unique molecular structures result in diverse roles and functions. For example, the dark eumelanins and the reddish-brown pheomelanins are the primary determinants of skin color and both generated by tyrosinase catalyzing conversion of tyrosine to dopaquinone, but the non-enzymatic incorporation of cysteine accounts for a switch of the eumelanin into sulfur-containing pheomelanin (ref. 2). Eumelanin has been known as primary antioxidant and photoprotective agent in dark-skinned phenotypes. In contrast, pheomelanin is photosensitive and tends to increase levels of reactive oxygen species (ROS), which has been implicated as a major culprit in melanoma and skin cancer of red-haired and fair-skinned populations. The nitrogen free 1,8-dihydroxynaphthalene (DHN)-melanin and pyomelanin are synthesized apparently exclusively in microorganisms (bacteria and fungi). DHN-melanin is catalyzed by six enzymes using endogenous acetyl CoA or malonyl CoA as precursor and pyomelanin is produced via degradation of tyrosine of L-tyrosine with homogentisic acid (HGA) as the main intermediate. Melanin produced by microorganisms confer a survival advantage in the environment by protecting against environmental predators, heavy metals toxicity, and physical insults such as UV and solar radiation (ref. 3). Melanin producing fungi are found widely distributed in Mir Spacecraft and the damaged nuclear reactor at Chernobyl, suggesting that synthesis of melanin is a self-defense mechanism for microbes to resist ionizing radiation (ref. 4).

Inspired by physicochemical, optoelectronic, self-assembly and adhesive properties of natural melanin, a number of research groups have synthesized melanin nanoparticles for a very broad range of applications including protective coating, functional films, environmental sensors and energy-storage devices (ref. 5). For example, rationally designed melanins with addition of a variety of precursors in the synthetic reactions were demonstrated to protect mammalian cells against ionizing radiation of different energies (ref. 6). The majority of melanin investigations to date have involved melanins either chemically synthesized or extracted from animals. Limited animal resources and cumbersome extraction procedures prevent their wide application. For chemically synthesized melanin, it is difficult to control catalysis, oxidation and assembly under confinement, a process that is not fully understood. Poorly defined chemical and structural compositions and insoluble and heterogeneous products limit the prior applications of these materials.

A need exists for new techniques for melanin production, which can make larger quantities of quality high-quality melanin available for applications such as adsorbent and barrier materials.

BRIEF SUMMARY

In one embodiment, a method of treating a fabric involves growing modified *Vibrio natriegens* bacteria in condition of expressing tyrosinase (monophenol monooxygenase EC 1.14.18.1) and thereby obtaining melanin from the bacteria, then immobilizing the melanin onto a fabric via a microwave process.

In another embodiment, a material comprises fabric in a state of being modified via microwave treatment, the fabric being chemically bonded to melanin.

In a further embodiment, a method of bonding melanin to fabric includes chemically treating a fabric to make it amenable to melanin binding; irradiating the treated fabric with microwave radiation; and bonding the melanin to the irradiated fabric.

BRIEF DESCRIPTION OF THE DRAWINGS

FIGS. 14A and 14B show results for capture and conversion of paraoxon (A) and dizainon (B) for melanin #1 in a

DETAILED DESCRIPTION

Definitions

Figure 1:
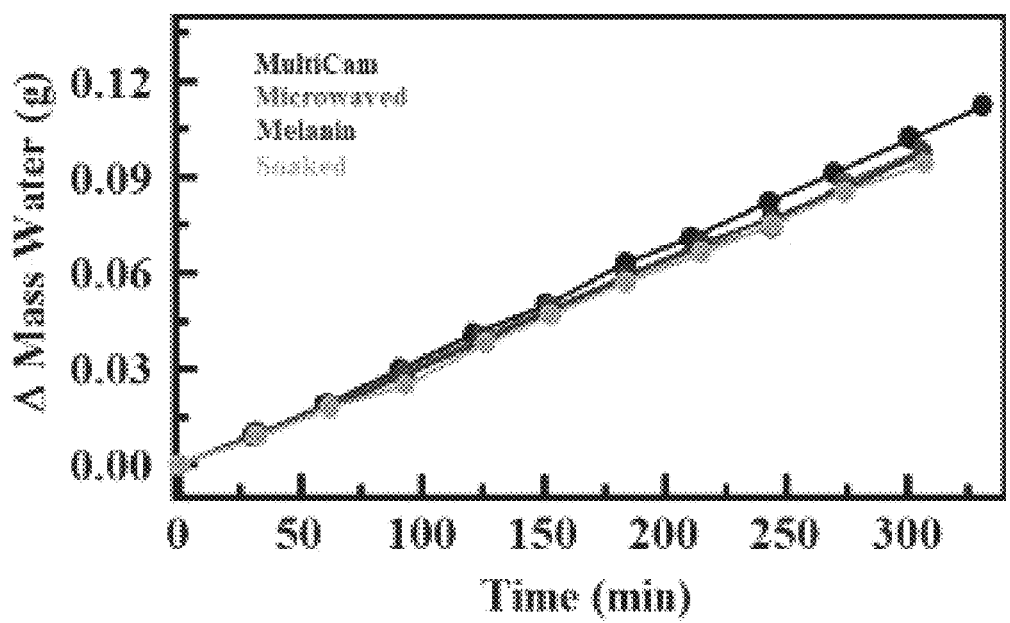
FIG. 1 displays data on water vapor permeation. Results from water vapor permeation analysis are presented for the complete melanin modified fabric (blue). Results for the MultiCam ACU fabric only (black), the silicate modified fabric (red), and a fabric soaked in melanin solution (orange) are presented for comparison.
Figure 2:
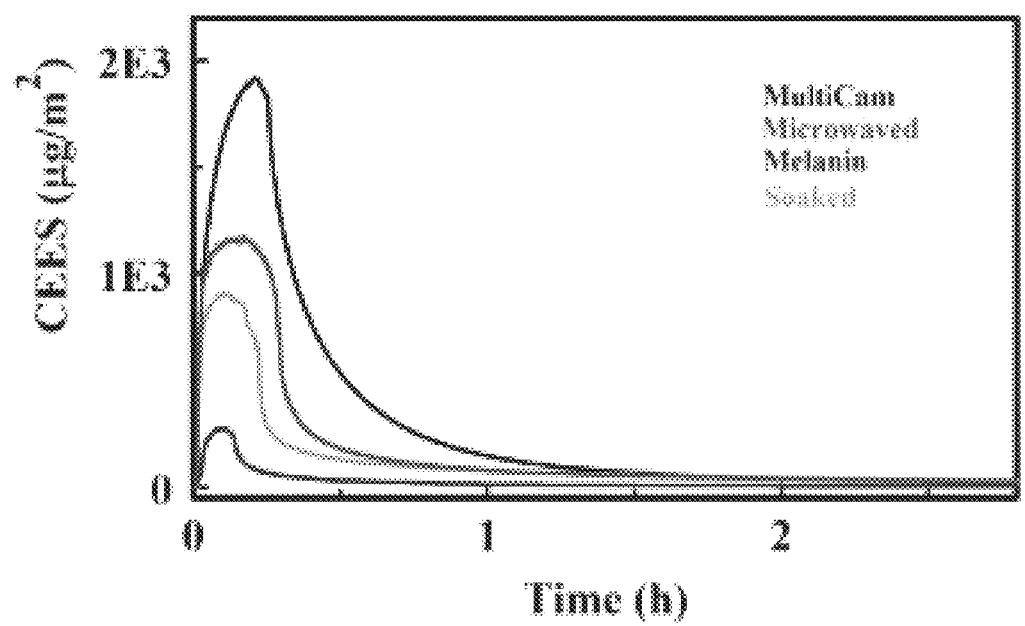
FIG. 2 shows permeation of 2-chloroethyl ethyl sulfide (CEES) through a complete melanin functionalized fabric is presented (blue) with the results for the fabric only (black), the microwave initiated fabric (red), and a fabric soaked in the melanin solution (orange).

Before describing the present invention in detail, it is to be understood that the terminology used in the specification is for the purpose of describing particular embodiments, and is not necessarily intended to be limiting. Although many methods, structures and materials similar, modified, or equivalent to those described herein can be used in the practice of the present invention without undue experimentation, the preferred methods, structures and materials are described herein. In describing and claiming the present invention, the following terminology will be used in accordance with the definitions set out below.

As used herein, the singular forms "a", "an," and "the" do not preclude plural referents, unless the content clearly dictates otherwise.

As used herein, the term "and/or" includes any and all combinations of one or more of the associated listed items.

As used herein, the term "about" when used in conjunction with a stated numerical value or range denotes somewhat more or somewhat less than the stated value or range, to within a range of ±10% of that stated.

Overview

Described herein is the application of melanin for providing adsorbent and barrier properties. A microwave initiated process for modification of fabrics using a melanin product produces a coating on the fibers that results in barrier properties for chemical targets. This is an example of a type of product as well as a type of immobilization method. Other products would include those for protection of solid surfaces (coatings) or air filtration media as well as dispersible adsorbents and adsorbents for decontamination of skin, clothing, solid surfaces, or water.

Biosynthesis of melanin with microbial systems offers a promising alternative to chemical synthesis of melanin or the harvest of melanin from animals. Since microorganisms (bacteria and fungi) are easily cultivated and economically sustainable, they have the great potential to produce the advanced biomaterials that can respond, sense and resist environmental stresses and generate electrical or chemical outputs. In addition, microbes could be used for large scale production through fermentation. Furthermore, because biosynthesis pathways of various melanins are well understood, synthetic biology becomes a powerful strategy to genetically manipulate organisms so as to modulate melanin compositions and structures, improve production yields and regulate biosynthesis with external signals.

Tyrosinase (monophenol monooxygenase EC 1.14.18.1), a copper-containing enzyme, has been reported to synthesize melanin in many microbial species (ref. 7), but this enzyme is not present in *Escherichia coli* or other model organisms. With recombinant DNA technology, the tyrosinase gene has been cloned and heterologously expressed in *E. coli*. Melanin production was optimized and characterized for a variety of applications. For example, the recombinant *E. coli* expressing tyrosinase at the cell membrane was demonstrated to synthesize and deposit melanin on the bacterial surface, resulting in creation of a black cell exterior. Such melanized bacteria showed superior absorption capacity by capturing 99% of a pharmaceutical wastewater pollutant, chloroquine (ref. 8)

The present inventors engineered the marine bacterium *Vibrio natriegens* to synthesize melanin by expressing a heterologous tyrosinase gene from *Bacillus megaterium*. *V. natriegens* is recognized as one of fastest growing organisms currently known with a doubling time less than 10 min. With nutritional versatility, rapid growth rate and lack of pathogenicity, it has become an attractive alternative to *E. coli* for synthetic biological applications (ref. 9). Melanin synthesis from *V. natriegens* could be regulated by various biochemical and optical stimuli and that the produced melanin could be found in cell-free supernatants as nanoparticles as well as associated with the cell membrane. The treatment of melanized bacteria with strong detergents and acids did not lyse cells but resulted in 'melanin ghost-like' structures. Free radicals in such bacterial melanin were demonstrated by electron paramagnetic resonance (EPR) signals, which were influenced by UV and gamma radiation. Melanized bacteria not only showed resistance to UV and hyper-osmolality but also were able to adsorb organic compounds such as chloroquine and trinitrotoluene (TNT) in a matter of minutes. Owing to its biocompatibility, scalability and physicochemical properties, melanin synthesized from the engineered bacteria represents a promising biomaterial in a broad range of applications.

EXAMPLES

Melanin

The tyrosinase gene from *Bacillus megaterium* Tyr1 was synthesized by Eurofins Genomics (Louisville, Ky.). The PCR amplified Tyr1 sequence was cloned into the plasmid pJV298, replacing the GFP gene with Gibson Assembly Master kit (New England Biolabs). The resulting plasmid pJV298-Tyr1 was propagated in *E. coli* NEB5α strain and then transformed into *V. natriegens* with electroporation method.

The modified *V. natriegens* (pJV-Tyr1) was inoculated into 3 ml of LM liquid medium supplemented with 6 mg/ml chloramphenicol (LM-Cm) to maintain the plasmid and grown at 30° C. overnight. 0.5 ml overnight culture was transferred into 50 ml LM-Cm medium and shaken at 200 rpm at 37° C. for 3 hours. Then tyrosinase production was induced by the addition of 200 μM isopropyl β-D-1-thiogalactopyranoside (IPTG) for 3 more hours.

50 ml LM-Cm culture was spun down at 5000 rpm for 10 min. Cell pellets were washed with 50 ml M9 minimal medium once and resuspended in 50 ml M9 medium supplemented with 50 μg/ml $CuSO_4$ and 0.4 mg/ml tyrosine. Cell suspension was shaken at 200 rpm at 30° C. and turned to black after 10 min incubation, indicating melanin production was initiated. To maximize melanin production, the culture was kept shaking at 30° C. for overnight. Melanized bacterial cells were harvested by centrifugation at 5000 rpm for 10 min. The black supernatant that contained melanin nanoparticles was passed through Millipore 0.2 μm polyethersulfone (PES) membrane for removing cell debris. The filtered melanin solution was used for the fabric modification experiments. Meanwhile, melanin particles could be aggregated and precipitated by adding 1 M HCl in the melanin supernatant.

The protocol for making bacterial "melanin ghosts" was modified from the method previously developed in fungi (ref. 10). Melanized bacteria were incubated with 10 ml 4 M Guanidinium thiocyanate at room temperature for 10 min. Cells were washed with deionized water once, hydrolyzed by adding with 6M HCl and boiled for 20 min, which completely solubilized cell structures. The resulting black particles, called "melanin ghosts", with melanin maintained in cell walls were washed with deionized water multiple times until pH reached 6.

Fabric Modification

Previous work at US Naval Research Laboratory focused on application of a microwave initiation technique for modification of fabrics using organosilicate sorbents, as described in U.S. Pat. No. 9,689,111 incorporated herein by reference for the purpose of disclosing techniques for fabric modification. Here, the idea was adapted to produce a fabric modified using melanin from a supernatant preparation. Microwave initiation of MultiCam ACU fabric used a solution of 10 ml, ammonium hydroxide (28-30%) with 184 mL of isopropanol in a glass beaker using a magnetic stir bar at 150 rpm. The primary amine groups were provided by 3-aminopropyltriethoxysilane (6 mL) added to the stirring solution [ref. 21]. The fabric was submerged in this solution and then microwaved at 1,200 W for 30 s. This submerge and microwave process was completed for a total of three cycles after which the fabric was dried at 100° C. overnight. Melanin was deposited on this fabric using 1-ethyl-3-(3-dimethylaminopropyl)carbodiimide (EDC 10 mg/cm fabric) in 0.1 M MES buffer pH 5.5 (2-(N-morpholino)ethansulfonic acid) (samples called covalent). This deposition used 0.79 mL of the provided melanin solution per cm of fabric (3.18 cm wide). The fabric in this solution was incubated overnight on a rotisserie mixer. Following incubation, fabric was rinsed repeatedly in deionized water and dried at 40° C. Melanin modification was also accomplished by simply soaking untreated fabric in the MES melanin solution (also at 0.79 mL/cm) with no EDC. This sample was drained well (not rinsed) and dried at 40° C. (samples called soaked).

The water vapor transport (WVT) rate for the treated fabrics was evaluated using a circular fabric sample with a total exposed area of 1.65 $cm^2$. (White, et al, 2018) This method follows the guidance provided by ASTM E96, Water Vapor Transport: Upright Open Cup Method to characterize water vapor transport through the fabric samples and uses an incubator modified to provide an enclosure at 25° C. A scintillation vial (20 mL) is loaded with 16.9 mL deionized water. The fabric sample is sealed over this vial, and vial is weighed. Desiccant drives a humidity differential in the incubator, and a dry nitrogen stream flows across the surface of the sample (0.25 L/min). The weight of the vial is measured at 30 to 45 min intervals using an analytical balance. As shown in FIG. 1, microwave initiation of the fabric caused a slight reduction in water vapor transport as compared to the untreated fabric. No significant changes in water vapor transport were noted following deposition of melanin on this initiated fabric. The WVT rate for the fabric was determined to be 123 $g/h/m^2$. The WVT rate was reduced to 115 $g/h/m^2$ upon microwave initiation and following soaking in melanin solution.

TABLE 1

Water Vapor Transport Rates for Evaluated Fabrics

| Material | Water Vapor Transport Rate ($g/h/m^2$) |
|---|---|
| MultiCam ACU fabric | 123 ± 4 |
| APS modified fabric | 115 ± 4 |
| Fabric soaked in melanin | 115 ± 4 |
| Covalent melanin modified fabric | 111 ± 4 |

The permeation of 2-chloroethyl ethyl sulfide (CEES), methyl salicylate (MES), and dimethyl methylphosphonate (DMMP) through fabric samples was evaluated using the guidance provided by Test Operations Procedure (TOP) 8-2-501, Permeation Testing of Materials with Chemical Agents or Simulants (Swatch Testing). (ECBC-TR-1141) An internal, probe driven heater was used to control the temperature within a custom environment. The ratio of humid to dry air entering this chamber is addressed using probe driven mass flow controllers. The stainless-steel aerosol-vapor-liquid-assessment group (AVLAG) cell holds the sample horizontally with O-ring seals. Diffusive permeation testing uses a nitrogen stream. The headspace above the swatch, in which the target is placed, is stagnant with no pressure difference above and below the swatch. The sample is supported between two solid support discs with aligned 0.64 $cm^2$ circular openings. This assembly is placed in the AVLAG cell, and humidity is equilibrated for 2 h. Target is introduced as liquid droplets using a repeating dispenser. A dedicated FID allows for continuous monitoring of target concentrations.

The apparatus for evaluation of target vapor permeation through fabric samples was based on the stations employed by the Chemical Technology Team (CTT) at Natick Soldier Research Development and Engineering Center (NSRDEC) (White, et al, 2018). The temperature in the custom environmental chamber is controlled using a probe inside the chamber which adjusts an Air-Therm ATX heater (World Precision Instruments). Mass flow controllers, regulated by an inline Vaisala humidity probe, govern the ratio of humid to dry air entering the chamber. An Aerosol Vapor Liquid Assessment Group (AVLAG) test cell is used for these evaluations. These cells are stainless steel and hold the sample horizontally with O-ring seals (refer to TOP 8-2-501). The AVLAG cell is set up for single flow diffusive penetration testing using a single air or nitrogen stream. The "headspace" above the swatch is stagnant, and the differential pressure above and below the swatch is zero. A sample (2.54×2.54 cm) is sandwiched between two supports with 0.64 $cm^2$ circular openings. The sample assembly is placed in the AVLAG cell and equilibrated to the desired humidity for 2 h. Target is introduced by placing liquid drops on top of glass wool using a repeating dispenser. Glass wool is used to help increase the volatility of the simulant. Challenge is applied to the surface of the sample in the static region of the AVLAG cell; therefore, evaporation is not a significant consideration. A direct line from the permeation cell to a dedicated FID (SRI model 110) allows for continuous monitoring of target concentrations. The FID uses Peak Simple, six-channel data acquisition software (SRI) for signal capture and peak integration. Excess flow from the direct line (above 50 mL/min) is filtered through a carbon scrubber.

Figure 5:
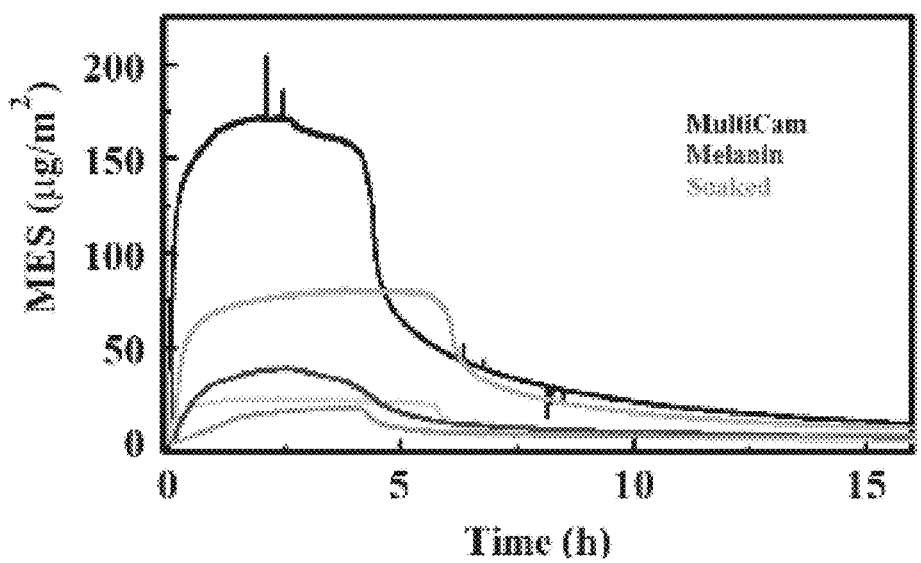
FIG. 5 shows permeation through wet fabrics. Permeation of MES through a complete melanin functionalized fabric is presented (blue) for the dry (light) and water saturated (dark) versions. Results for the soaked fabric (orange) are also provided for the dry (light) and water saturated (dark) versions. Results for the fabric only (black) are also included.

CEES and MES are simulants commonly used for HD mustard, a blister agent. CEES provides similar reactive pathways to the agent while MES provides similar penetrating properties. DMMP provides a simulant for phosphorous containing nerve agents. FIG. 5 provides the time-dependent FID response for CEES on the melanin functionalized fabric as well as controls comprised of fabric only, microwave initiated fabric, and melanin soaked fabric. Results are also summarized in Table 2. The threshold for initial target breakthrough used here is based on the 1 h marginal exposure level in air (military exposure guideline, MEG). A hazard level qualified as "marginal" is defined as causing degraded mission capability or unit readiness on the basis of the proportion of the unit likely to exhibit effects, the nature of those effects, and confidence in the available data. The 1 h marginal air exposure limit for CEES is 0.1 $mg/m^3$. While initiation of the fabric did not extend the initial period prior to breakthrough of target, the peak rate of target transport through the fabric was reduced (34.5 $g/m^2/h$ for untreated fabric and 21.2 $g/m^2/h$ for initiated fabric). Addition of melanin to this initiated fabric further reduced the peak rate of transport to 5.0 $g/m^2/h$. The melanin functionalized fabric reduced total CEES permeation by an order of magnitude over the 1,000 min experiment period. In comparison, the melanin soaked fabric reduced the peak rate of transport to 16.4 $g/m^2/h$ and total target permeation to 574 µg, 54% of that observed for the untreated fabric.

Figure 3:
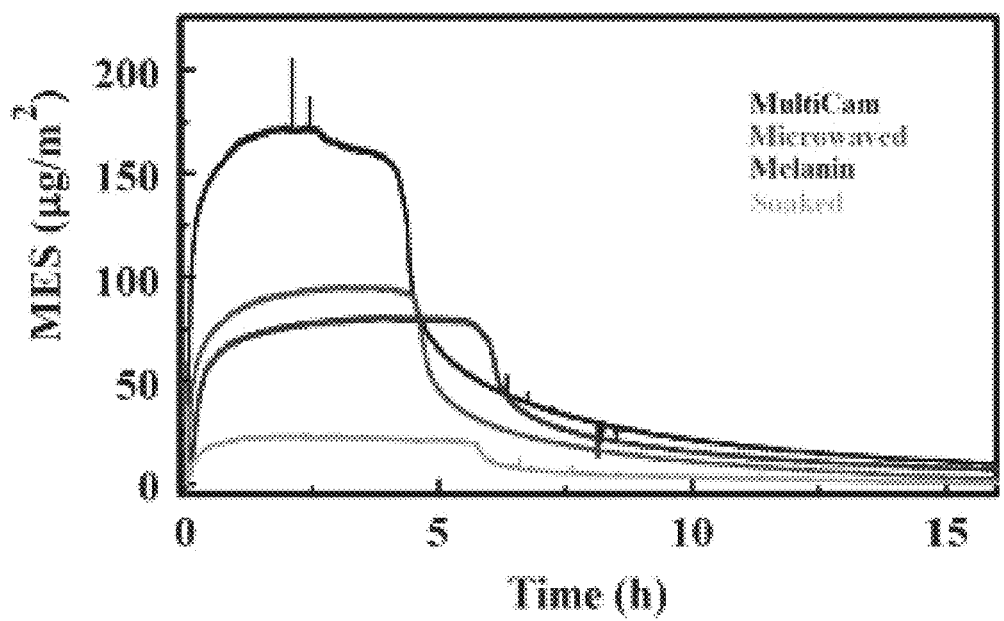
FIG. 3 provides data for permeation of methyl salicylate (MES). Permeation of MES through a complete melanin functionalized fabric is presented (blue) with the results for the fabric only (black), the microwave initiated fabric (red), and a fabric soaked in the melanin solution (orange).
Figure 4:
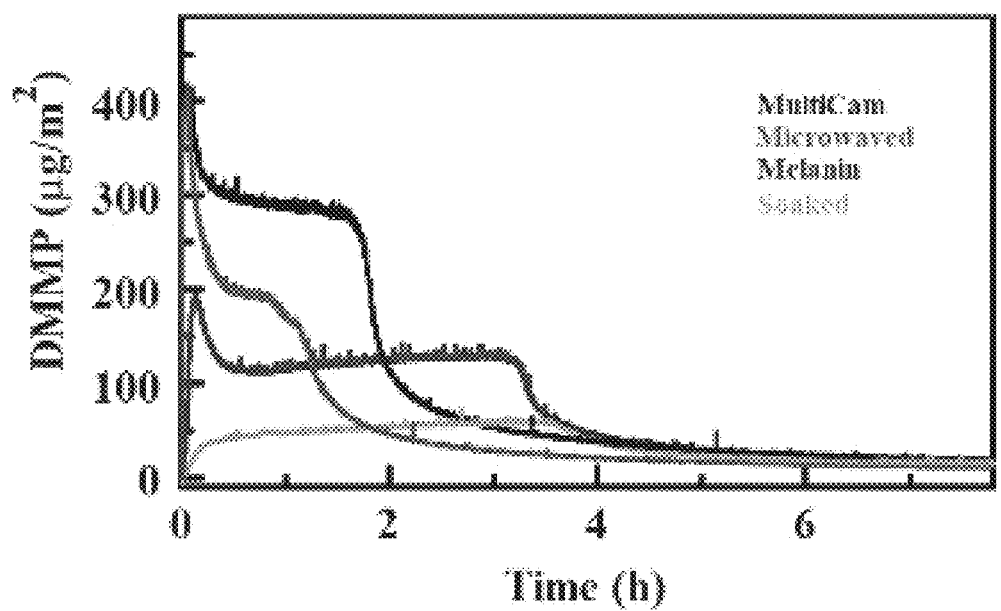
FIG. 4 shows permeation of dimethyl methylphosphonate (DMMP). Permeation of DMMP through a complete melanin functionalized fabric is presented (blue) with the results for the fabric only (black), the microwave initiated fabric (red), and a fabric soaked in the melanin solution (orange).
Figure 6A:
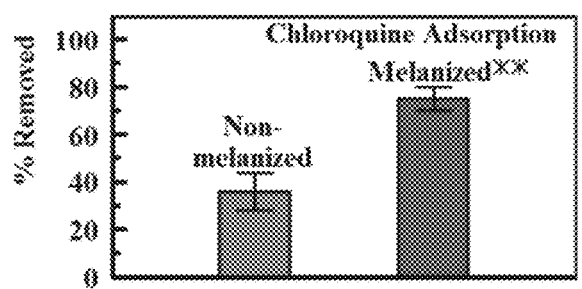
FIGS. 6A and 6B display data on adsorption of chloroquine and TNT by melanin-producing *V. natriegens* cells. Removal of chloroquine from PBS by non-melanized (gray) and melanized cells (red) (FIG. 6A); TNT adsorption to melanized cells at 5, 10 and 30 min (FIG. 6B).
Figure 6B:
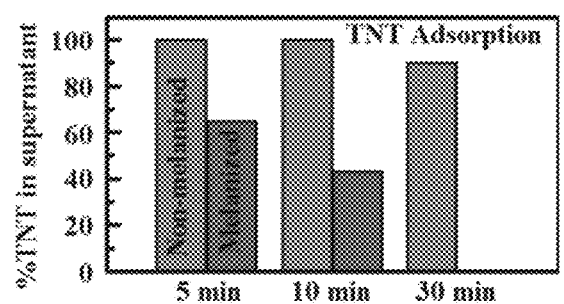

Under methyl salicylate (IVIES) challenge, initial breakthrough the MultiCam ACU fabric was observed at 1.1 min (FIG. 6). None of the treatments had a significant impact on the pre-breakthrough duration. Microwave initiation of the fabric reduced the peak rate of MES transport from 3.7 to 1.7 $g/m^2/h$. Addition of melanin to this fabric further reduced peak transport to 1.4 $g/m^2/h$. The total target transported through the fabric was similarly impacted with only 26% of that observed for the untreated fabric recovered during exposure of the melanin functionalized fabric. Soaking the fabric in melanin solution resulted in greater impact on both the total recovered target (15%) and the peak rate of transport (0.7 $g/m^2/h$). CEES is known to undergo hydrolysis on contact with water while MES is stable. The differences noted in reduction of MES transport as compared to that of CEES through the melanin functionalized fabric may be related to the different mechanisms possible in these materials and the availability of water in the different fabric samples. As shown in the photographs of FIG. 3, the covalently modified material appears to bear significantly more melanin than the soaked sample.

TABLE 2

Summary of Results for Characterization of Fabrics

| Material | Initial Breakthrough (min) | Peak Rate ($g/m^2/h$) | Total (µg) over 1,000 min |
|---|---|---|---|
| 2-Chloroethyl ethyl sulfide (CEES) | | | |
| MultiCam ACU fabric | 0.64 | 34.5 | 1070 |
| APS modified fabric | 0.50 | 21.2 | 705 |
| Fabric soaked in melanin | 0.84 | 16.4 | 574 |
| Covalent melanin modified fabric | 0.54 | 5.0 | 108 |
| Methyl salicylate (MES) | | | |
| MultiCam ACU fabric | 1.14 | 3.7 | 1170 |
| APS modified fabric | 1.13 | 1.7 | 651 |
| Fabric soaked in melanin | 1.89 | 0.7 | 181 |
| Covalent melanin modified fabric | 1.13 | 1.4 | 308 |
| Dimethyl methylphosphonate (DMMP) | | | |
| MultiCam ACU fabric | 0.62 | 7.5 | 1020 |
| APS modified fabric | 0.60 | 7.5 | 552 |
| Fabric soaked in melanin | 16.3 | 1.3 | 429 |
| Covalent melanin modified fabric | 3.62 | 3.5 | 734 |

Figure 7:
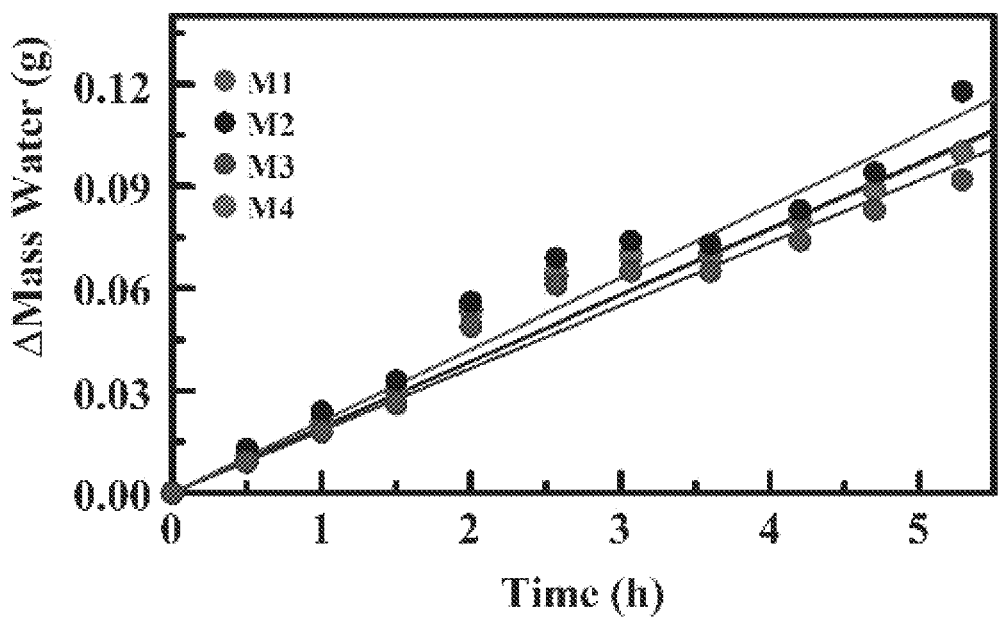
FIG. 7 shows water vapor transport measurements for fabrics treated with four different melanin preparations.

The 1 h marginal air exposure limit for DMMP is 500 $mg/m^3$; (ref. 11) none of the materials evaluated permitted target breakthrough at this rate. In order to provide a point of comparison, 5.0 $mg/m^3$ was used as the threshold value for DMMP analysis. The peak DMMP rate through the MultiCam fabric was 7.5 $g/m^2/h$ with initial breakthrough at <1 min and 1020 µg recovered over the 1,000 min experiment duration. Initiation of this fabric had no impact on initial breakthrough or peak transport rate, though total transport was significantly reduced (552 µg; FIG. 7). Addition of melanin to the initiated fabric extended the initial breakthrough duration to 3.6 min and reduced peak transport rate to 3.5 $g/m^2/h$. The profile of the breakthrough was, however, significantly changed, and total target recovered increased to 734 µg. The fabric soaked in melanin solution yielded an initial breakthrough period of 16.3 min with peak transport rate 1.3 $g/m^2/h$ and total permeated target of 429 µg. These results may further support differences in the availability of water in the materials. DMMP is miscible with water; MES is soluble at 0.64 g/L. Greater water content could help these targets pass through the barrier while reacting with the CEES to provide an effective reduction in total recovered.

Figure 8:
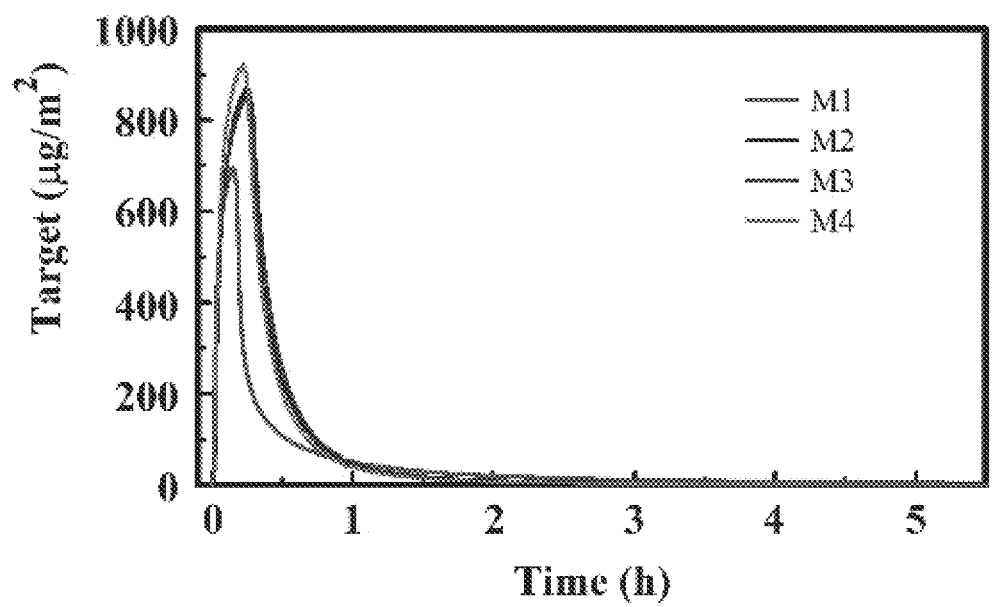
FIG. 8 provides the time-dependent flame ionization detector (FID) response for CEES on the four melanin-functionalized fabrics.

The impact of hydration was considered using similar experiments and samples of fabrics from the same preparation as those utilized above. Samples of the soaked and covalent melanin modified fabrics were saturated with deionized water overnight to fully hydrate the bound material. These 'wet' versions of the fabrics were subjected to AVLAG analysis using MES as the target (FIG. 8). Wetting of the covalently modified fabric resulted in reduction of the peak permeation rate from 1.4 $g/m^2/h$ to 0.7 $g/m^2/h$ with the initial breakthrough period extended from 1.1 min to 5.6 min (Table 3). Hydration of the melanin soaked sample showed an increase in the initial period from 1.9 min to 10.8 min with peak permeation rate reduced from 0.7 $g/m^2/h$ to 0.3 $g/m^2/h$. In both cases, the total target detected over the 1,000 min experiment was reduced. Beyond indicating that environmental conditions may be critical to predicting the performance of melanin modified materials, this result is interesting in the striking difference when compared to carbon based systems. In general, when a carbon based sorbent is wet, it ceases to function. The pore volume is filled by water allowing the target to pass through the spaces between the carbon granules or fibers. The results noted here would tend to indicate that applications using melanin would benefit from high humidity or even the presence of liquid water.

TABLE 3

Results for MES Evaluation of Wet and Dry Fabrics

| Material | Condition | Initial Breakthrough (min) | Peak Rate (g/m²/h) | Total (µg) over 1,000 min |
|---|---|---|---|---|
| Fabric soaked in melanin | Wet | 10.8 | 0.3 | 125 |
|  | Dry | 1.89 | 0.7 | 181 |
| Covalent melanin modified fabric | Wet | 5.59 | 0.7 | 247 |
|  | Dry | 1.13 | 1.4 | 308 |

Figure 9:
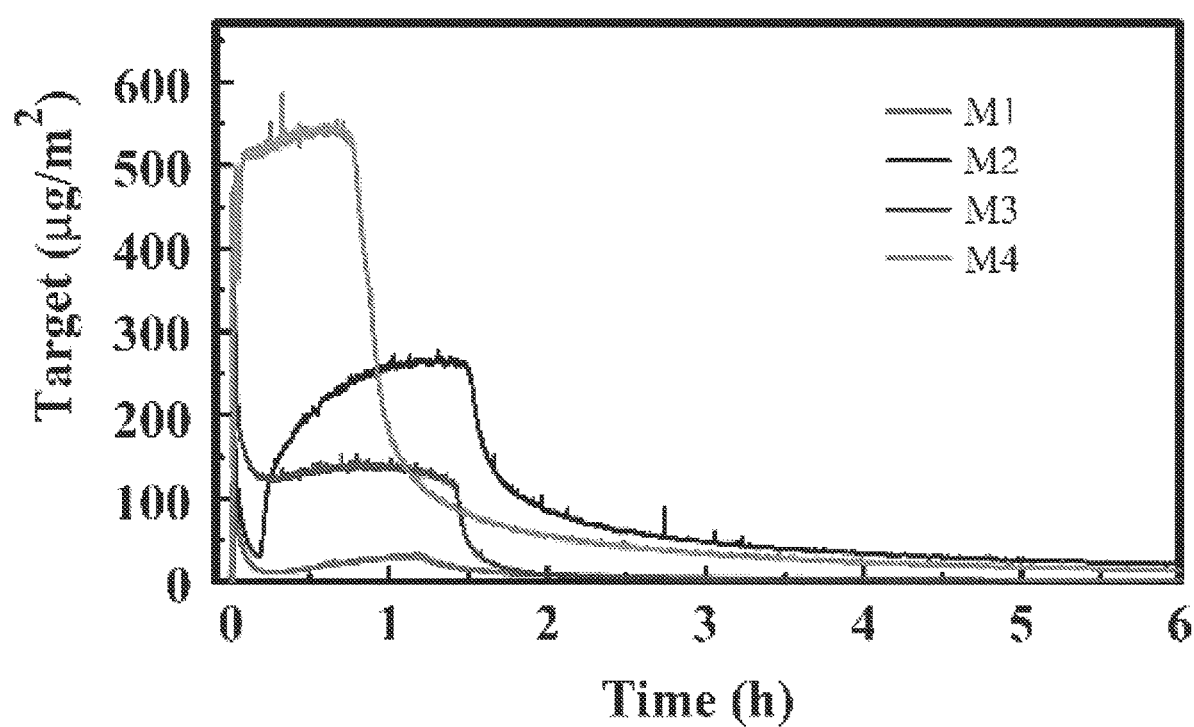
FIG. 9 has data on permeation of DMMP through different melanin functionalized fabrics.

Melanin exhibits diverse binding potential as a result of its complex polymeric structure. This makes melanin-producing bacteria valuable as potential candidate materials for bioremediation applications. Thus it was desired to explore the ability of melanin-producing *V. natriegens* to bind and sequester environmental contaminants. Melanin-producing *E. coli* was previously shown to effectively bind the toxic, antimalarial drug chloroquine in a pH-dependent manner, with less binding under acidic conditions (8). Similarly, melanin-producing *V. natriegens* was able to bind and sequester nearly 90% of the chloroquine from a 100 µM solution in PBS (FIG. 9).

TNT is another common environmental contaminant can be bound by melanin. Melanin-producing *V. natriegens* was added to a solution of TNT with a final concentration of 125 ppb in PBS and observed that cells could bind and remove most of the compound from solution. This process was time dependent, with only ~25% of TNT being removed after a 5 min incubation, but nearly 100% removal after a 30 min incubation (FIG. 9). It was also independent of cell viability, as cells heated to 60° C. for 20 min, which resulted in a complete loss of viability, produced similar results. Additionally, binding of TNT was pH-dependent, with the efficiency of TNT removal from solution going from nearly 100% removal at pH 6, to 80% at pH5, to only 10% at pH4. This suggests that melanin-producing *V. natriegens* cells are able to bind a variety of substances and that removal and degradation of compounds of interest from cultures can be done by changing the pH of the aqueous environment.

Further Investigations with Pheomelanin and Eumelanin

Additional studies were conducted using a variety of melanins, identified as melanin numbers 1 through 4. Melanin #1 is a pheomelanin produced by catalyzing L-DOPA and cysteine with tyrosinase in vitro. Melanin #2 was chemically synthesized and appears to be pheomelanin according to electron paramagnetic resonance analysis, though this is not completely certain. Melanin #3 is eumelanin purchased from Sigma-Aldrich. Melanin #4 is from the bacterium *Vibrio natriegens* that contained the engineered tyrosinase catalyzed L-DOPA and cysteine and produced brown color pigment in cell culture. After bacterial cells were spun down with centrifugation, the brown color supernatant was collected. Preliminary experiment indicated that this supernatant might be pheomelanin or mixture of pheomelanin and eumelanin.

These melanin variants were deposited on the amine functionalized fabric as described above. This deposition used 10 µL of the relevant melanin solution per cm² of fabric. A typical concentration of melanin solution was 2.3 mg/ml.

The water vapor transport (WVT) rate for the treated fabrics was evaluated using the guidance provided by ASTM E96, Water Vapor Transport: Upright Open Cup Method as described above. As shown in FIG. 7, no significant changes in water vapor transport were noted following deposition of melanin.

FIG. 8 provides the time-dependent FID response for CEES on the melanin functionalized fabrics. Results are also summarized in Table 4. Addition of melanin to this initiated fabric further reduced the peak rate of transport to 5.0 g/m²/h. All of these melanin functionalized fabric reduced total CEES permeation as well as peak permeation rate as compared to the microwave initiated fabric. None of the functionalizations extended the time prior to initial breakthrough. Melanin #1 provided the most significant reductions in total permeation and peak rate. Melanin #1 also produced significant reduction in peak and total permeation rates for DMMP. Melanin #4, on the other hand, had a negative impact on DMMP permeation (FIG. 9, Table 4). Melanin #2 had a low peak rate, but ultimately, allowed more of the DMMP to penetrate the fabric. Overall, Melanin #1 provided the best performance in permeation tests for both of the considered targets.

TABLE 4

Summary of Results for Characterization of Fabrics

| Material | Initial Breakthrough (min) | Peak Rate (g/m²/h) | Total (µg) over 1,000 min | Water Vapor Transport Rate (g/h/m²) |
|---|---|---|---|---|
| 2-Chloroethyl ethylsulfide (CEES) | | | | |
| Melanin #1 | 0.50 | 12.5 | 306 | 127 ± 4 |
| Melanin #2 | 0.50 | 15.7 | 405 | 117 ± 3 |
| Melanin #3 | 0.53 | 15.4 | 448 | 111 ± 2 |
| Melanin #4 | 0.50 | 16.6 | 408 | 117 ± 3 |
| APS modified fabric | 0.50 | 21.2 | 705 | 115 ± 4 |
| Dimethyl methylphosphonate (DMMP) | | | | |
| Melanin #1 | 1.81 | 3.1 | 71.1 | |
| Melanin #2 | 0.91 | 5.0 | 768 | |
| Melanin #3 | 0.48 | 8.4 | 223 | |
| Melanin #4 | 0.58 | 14.1 | 861 | |
| APS modified fabric | 0.60 | 7.5 | 552 | |

Beyond characterization of functionalized fabrics, the behavior of the melanin derivatives was considered in solution. These experiments used the various melanin compounds in aqueous solution with organophosphate pesticides in the presence and absence of illumination. Here, eumelanin is expected to be photoprotective while pheomelanin has been shown to be associated with phototoxic effects [ref. 26]. Melanin solution (5 µL; 11.5 µg) was mixed with target in aqueous solution (50 ppm). The solutions were divided into aliquots with half protected by aluminum foil and half exposed to illumination. All of the samples were placed under a solar simulating light source (Nova Extreme Pro High Output T5 Lighting System). At the indicated time points, an aliquot of both the illuminated and protected samples were removed, filtered (0.2 µm PTFE syringe filter), and the target remaining in solution was analyzed by HPLC. For paraoxon and diazinon analysis, a Shimadzu High Performance Liquid Chromatography (HPLC) system with dual-plunger parallel flow solvent delivery modules (LC-20AD) and an auto-sampler (SIL-20AC; 40 µL injection volume) coupled to a photodiode array detector (SPD-M20A; 277 nm) was used. The stationary phase was a C18 stainless steel analytical column (Luna, 150 mm×4.6 mm, 3 µm diameter; Phenomenex, Torrance, Calif.) with an isocratic 45:55 acetonitrile: 1% aqueous acetic acid mobile phase (1.2 mL/min) [ref. 27].

Figure 10A:
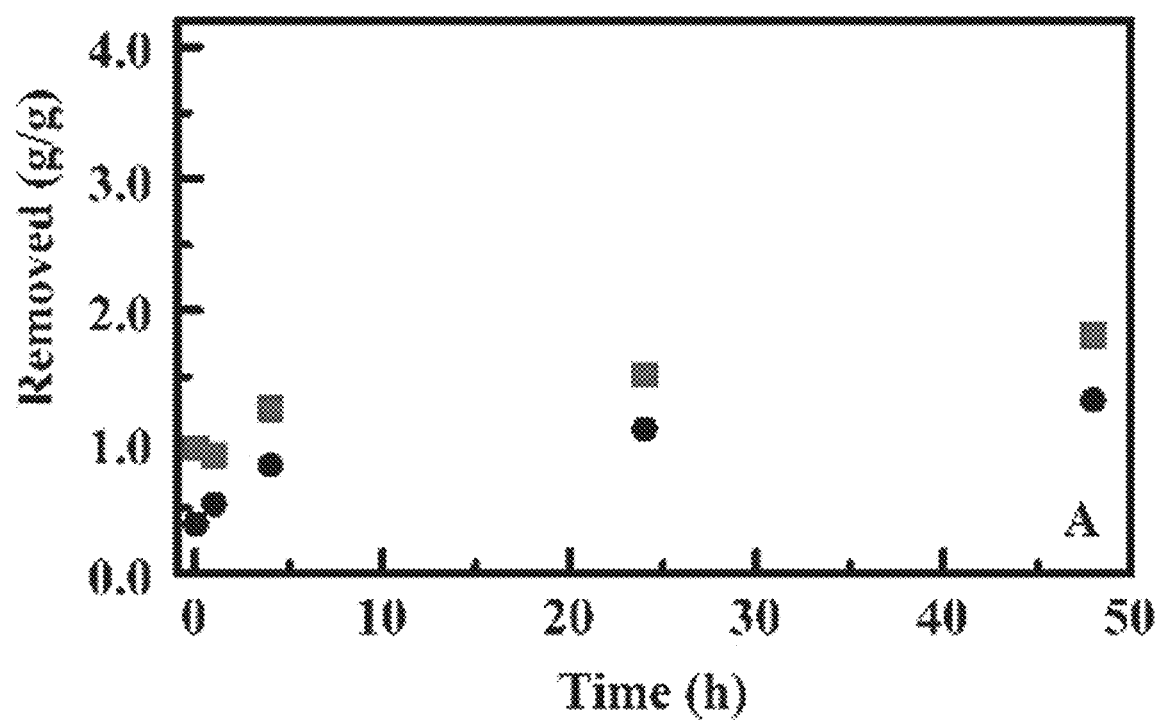
FIGS. 10A and 10B show data on the capture and conversion of paraoxon (A) and dizainon (B) by melanin #1 in aqueous solution, for illuminated and dark samples.
Figure 10B:
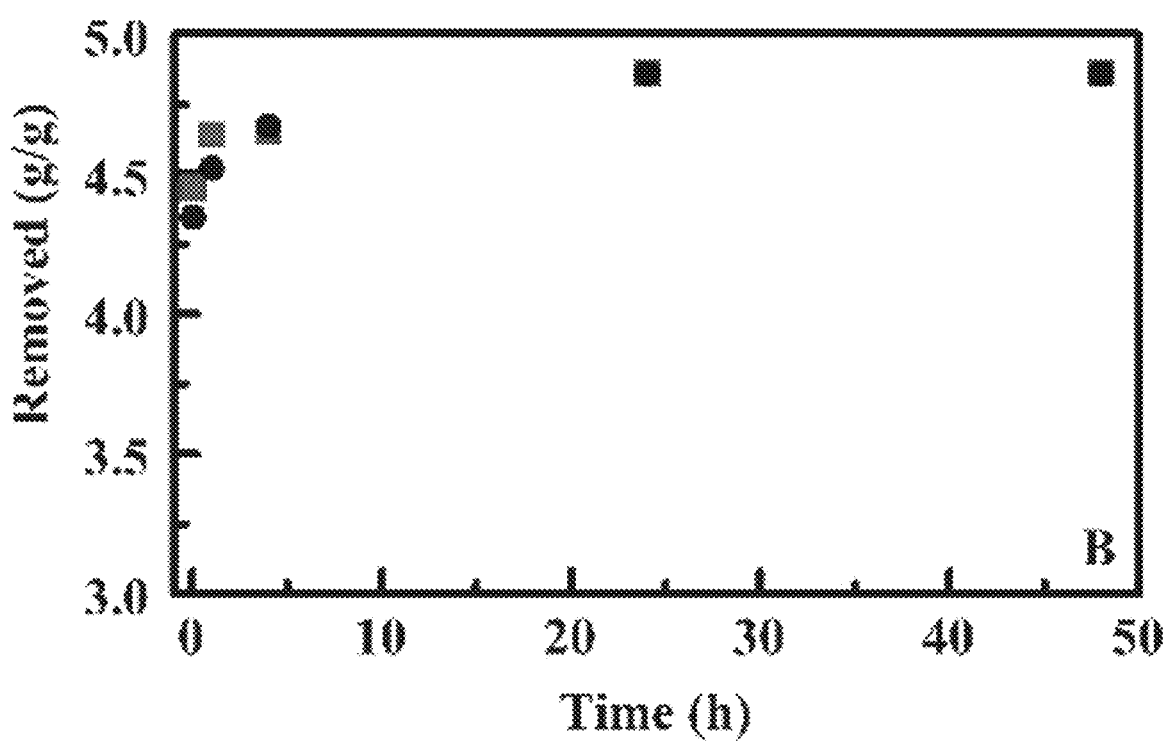
Figure 11A:
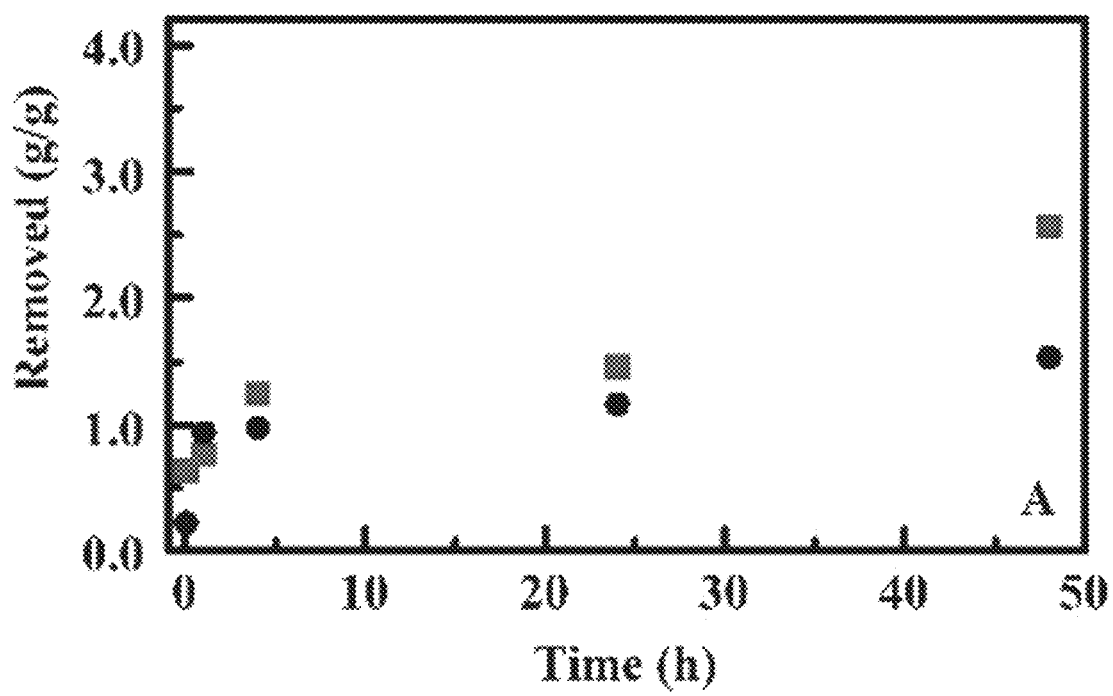
FIGS. 11A and 11B provide data on the capture and conversion of paraoxon (A) and dizainon (B) by melanin #2 in aqueous solution, for illuminated and dark samples.
Figure 11B:
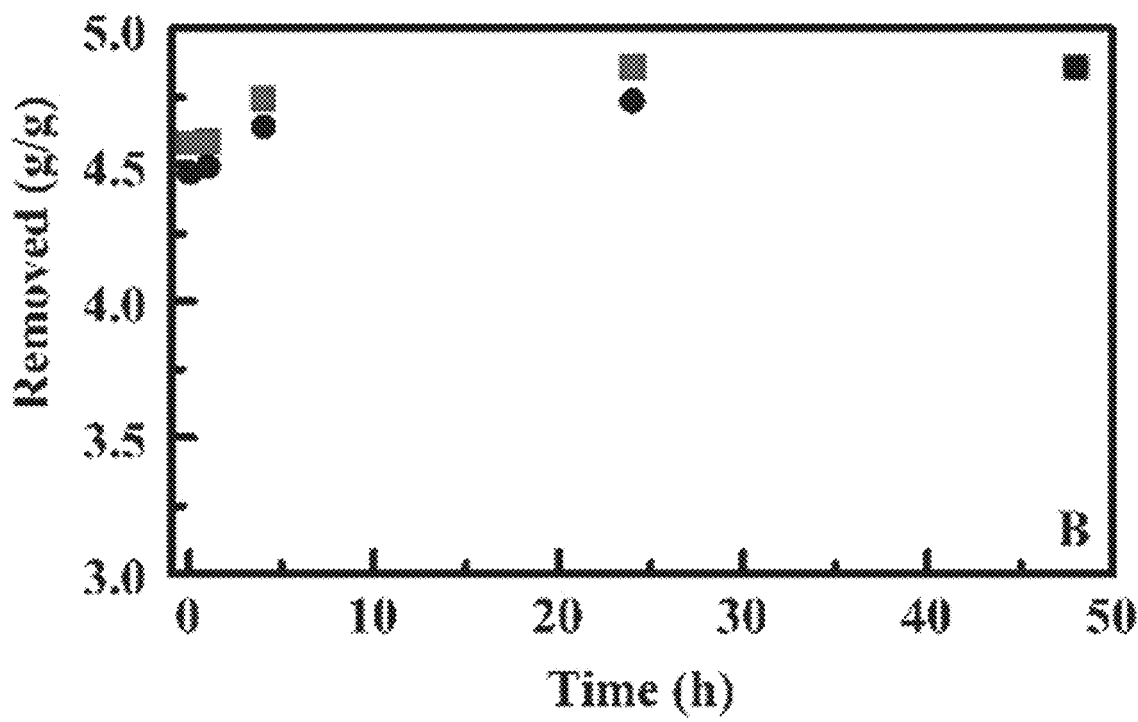
Figure 12A:
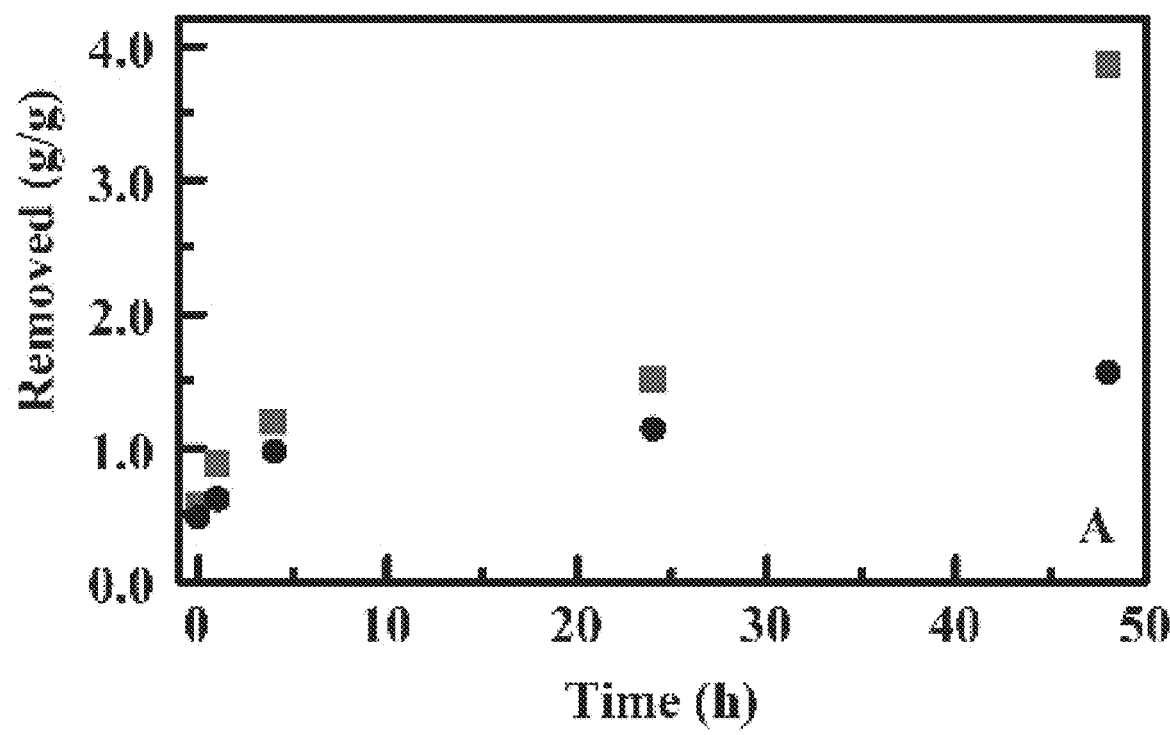
FIGS. 12A and 12B display data on the capture and conversion of paraoxon (A) and dizainon (B) by melanin #3 in aqueous solution, for illuminated and dark samples.
Figure 12B:
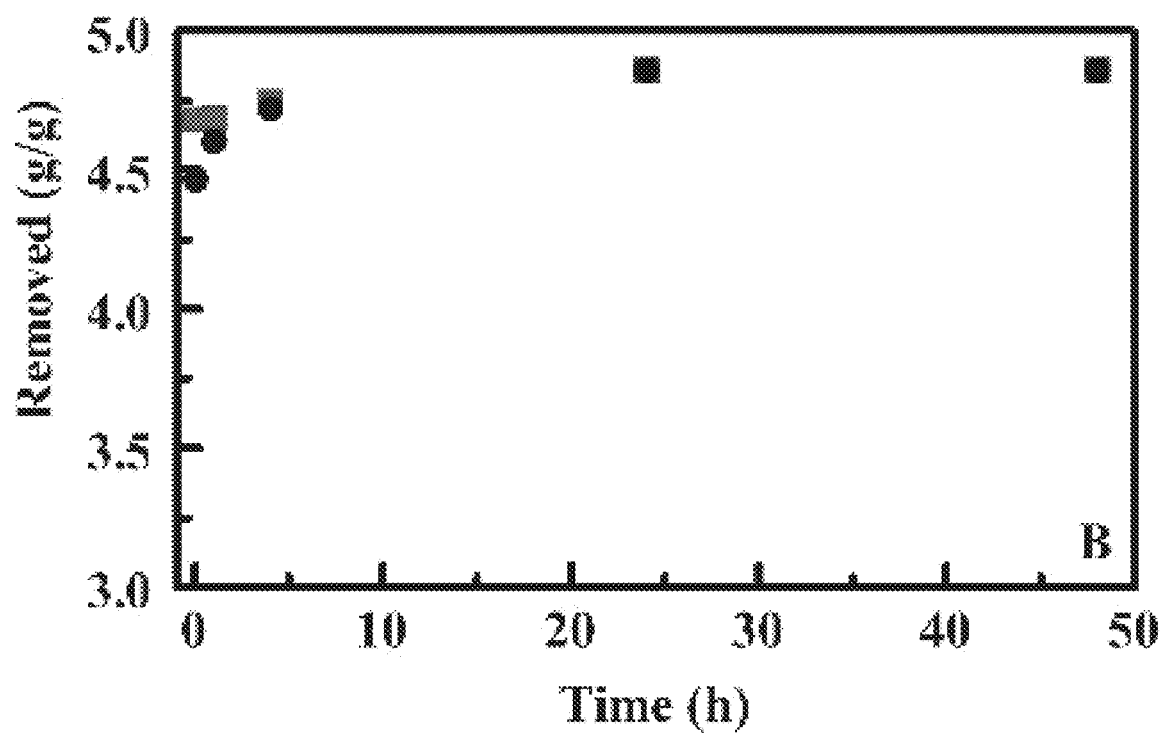
Figure 13A:
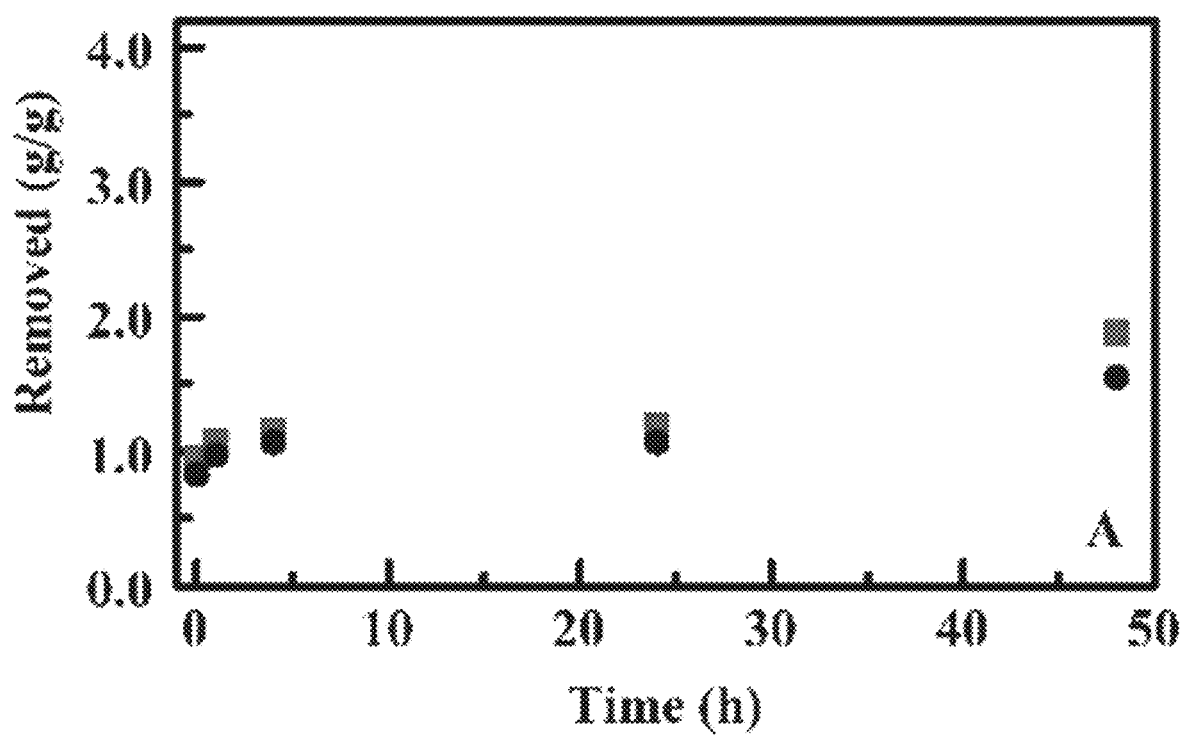
FIGS. 13A and 13B present data on the capture and conversion of paraoxon (A) and dizainon (B) by melanin #4 in aqueous solution, for illuminated and dark samples.
Figure 13B:
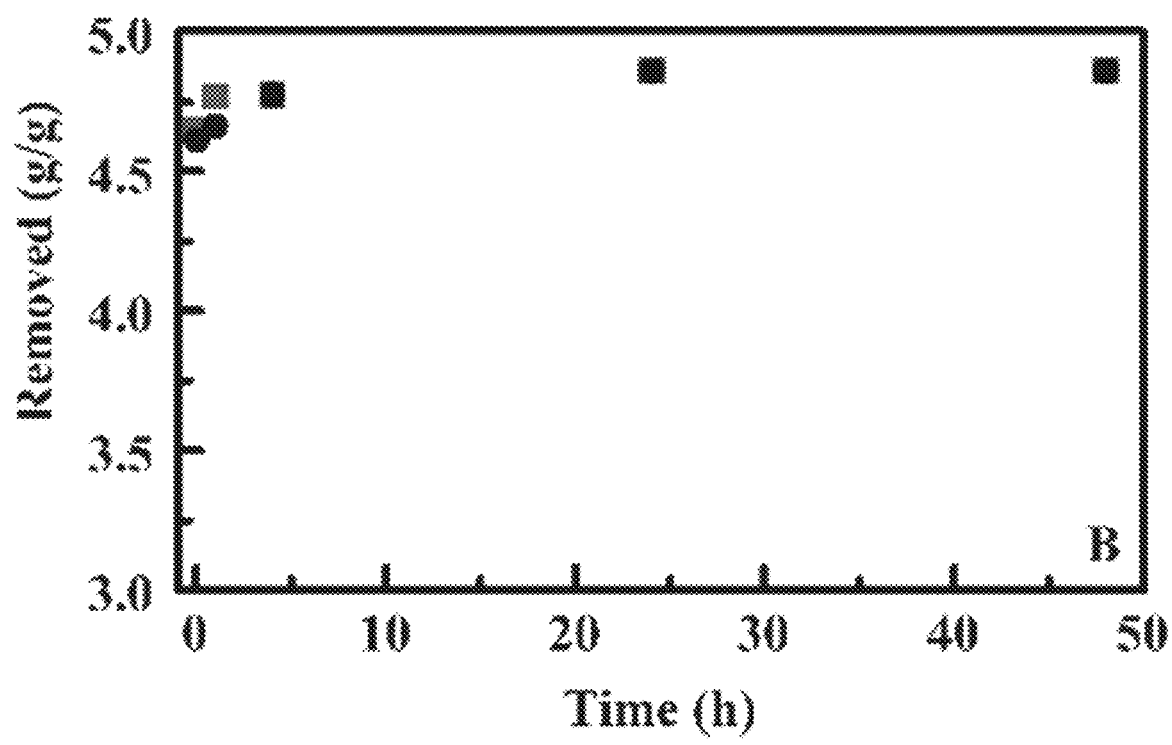

FIG. 10 presents results for evaluation of Melanin #1 in solution with paraoxon and diazinon. As shown, approximately 380 mg/g paraoxon is removed from solution upon interaction with the melanin. As time passes, the amount of paraoxon removed increases in both the dark and illuminated sample (4.8 g/g initially). The rate of removal by the illuminated sample is, however, faster than that noted for the sample without illumination. For diazinon, 4.35 g/g is removed from solution upon interaction with the melanin. This is likely influenced by the solubility of diazinon [ref. 28]. Both the illuminated and dark samples remove all diazinon from solution in less than 24 h. Melanin #2 (FIG. 11) showed similar paraoxon removal behavior over the first 24 h, but removal continued throughout the 48 h of the experiment. Diazinon removal was slightly slower for Melanin #2 than for Melanin #1. Diazinon capture and removal was similar for melanin #3 and #4. Paraoxon removal by Melanin #3 (FIG. 12) was similar up to the 24 h point; however, the 48 h point is significantly greater (3.86 g/g) than that of Melanin #2 (2.56 g/g). Paraoxon removal by Melanin #4 was similar to removal by Melanin #1 in the absence of illumination (FIG. 13).

Figure 14A:
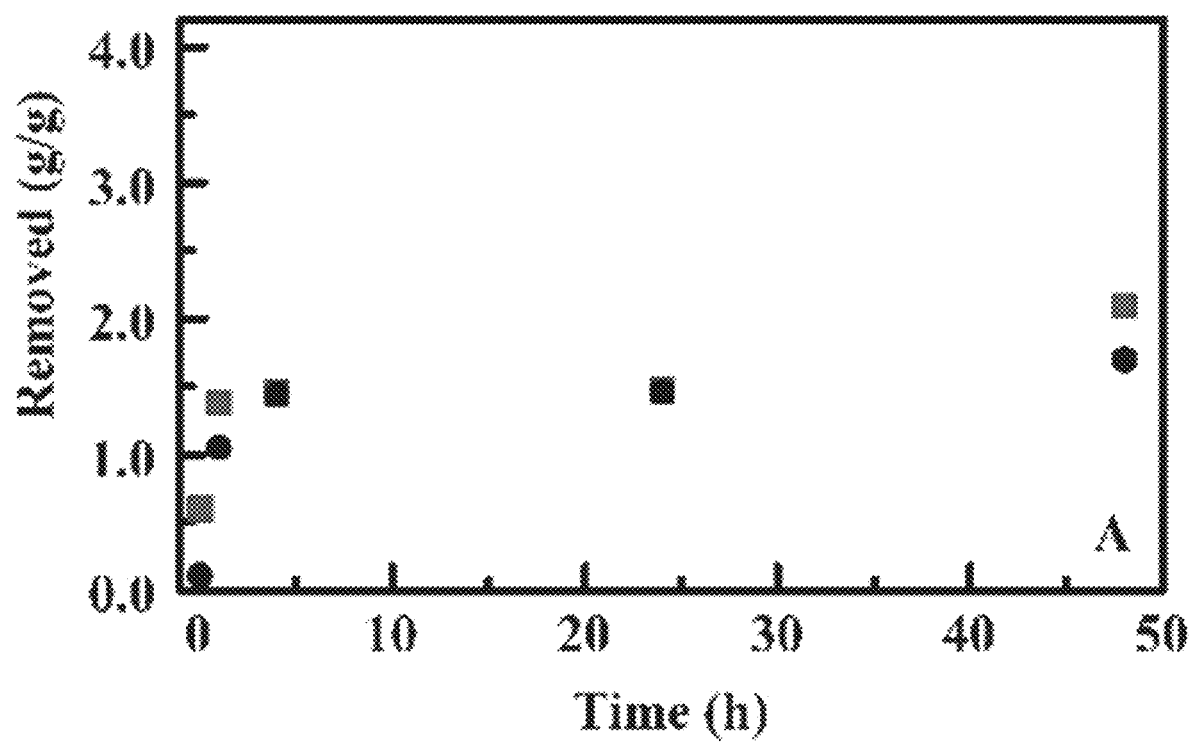
Figure 14B:
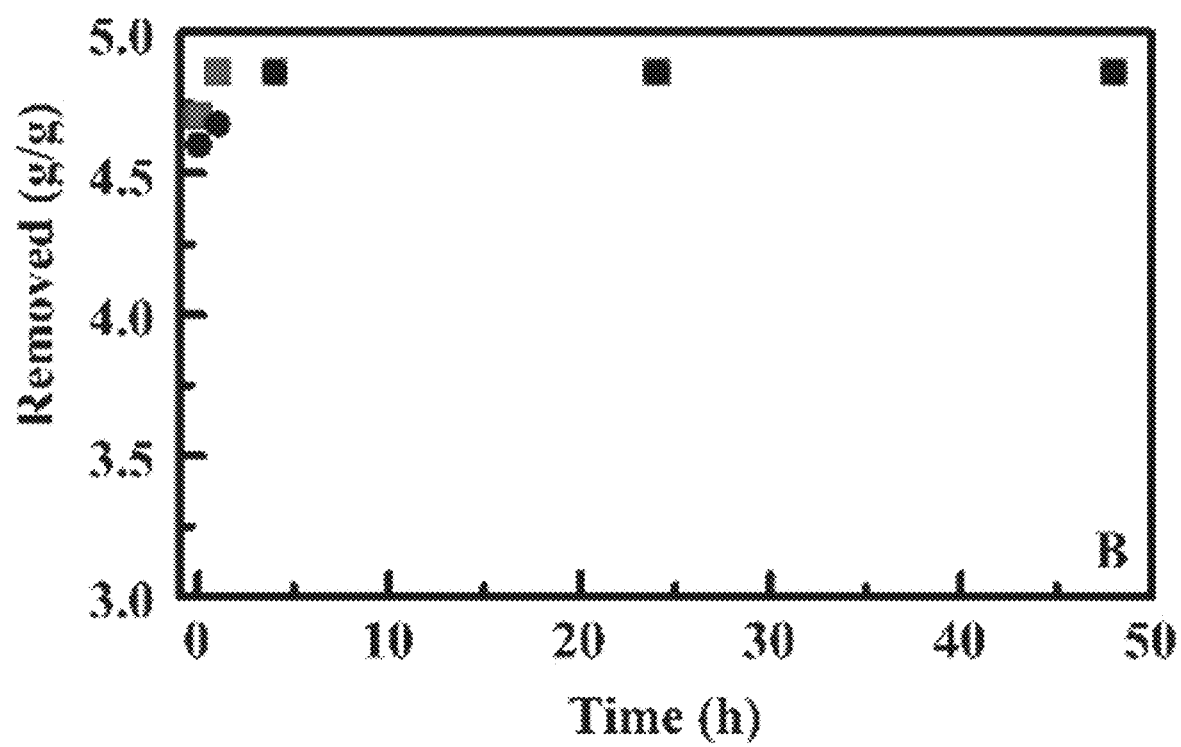

For comparison, the interaction of the targets in solution with the harvested supernatant solution from Melanin #4 was also evaluated, with data shown in FIG. 14. This shows diazinon results similar to those noted for the other variants. Paraoxon results for the supernatant were similar to those of Melanins #1 and #4. It is likely that little to none of this behavior is related to generation of reactive species by the melanin; it is more likely that these results are binding of the targets by the melanin and background breakdown of the targets. Melanin #2 and #3, on the other hand, appear to show catalytic activity Advantages Melanin offers the potential for new protective and decontaminating applications. Protective applications could include fabrics, air filtration, or adsorbents. Decontamination scenarios would likely be as adsorptive materials. The wide variety of molecular and morphological structures offer possibilities for tunable function that have not yet been explored. The described demonstrations could be applied to the generation of garments, shelters, or pleated filtration materials. A particular advantage of melanin is that it can be produced using a biological reactor system that may have a significant cost advantage over synthetic materials suitable to similar applications.

Traditional protective garments and shelters utilize carbon materials. These materials are typically reliant on non-specific adsorption, may provide little to no catalytic/reactive activity, and do not protect against the full range of threat agents. Often protective garments provide little to no water transport across protective barriers resulting in increased discomfort and limited operation duration. The materials described here may address some of these shortcomings. In addition, the flexibility of the format provides the opportunity for combining the approach with classical materials to improve their performance.

CONCLUDING REMARKS

Although the present invention has been described in connection with preferred embodiments thereof, it will be appreciated by those skilled in the art that additions, deletions, modifications, and substitutions not specifically described may be made without departing from the spirit and scope of the invention. Terminology used herein should not be construed as being "means-plus-function" language unless the term "means" is expressly used in association therewith.

REFERENCES

1. Meredith, P., and Sarna, T. (2006) The physical and chemical properties of eumelanin. Pigment Cell Res 19, 572-594
2. Micillo, R., Panzella, L., Koike, K., Monfrecola, G., Napolitano, A., and d'Ischia, M. (2016) "'Fifty Shades' of Black and Red or How Carboxyl Groups Fine Tune Eumelanin and Pheomelanin Properties." Int J Mol Sci 17
3. Eisenman, H. C., and Casadevall, A. (2012) Synthesis and assembly of fungal melanin. Appl Microbiol Biotechnol 93, 931-940
4. Dadachova, E., and Casadevall, A. (2008) Ionizing radiation: how fungi cope, adapt, and exploit with the help of melanin. Curr Opin Microbiol 11, 525-531
5. Kim, Y J., Khetan, A., Wu, W, Chun, S. E., Viswanathan, V., Whitacre, J. F., and Bettinger, C. J. (2016) Evidence of Porphyrin-Like Structures in Natural Melanin Pigments Using Electrochemical Fingerprinting. Adv Mater 28, 3173-3180
6. Schweitzer, A. D., Howell, R. C., Jiang, Z., Bryan, R. A., Gerfen, G., Chen, C. C., Mah, D., Cahill, S., Casadevall, A., and Dadachova, E. (2009) Physico-chemical evaluation of rationally designed melanins as novel nature-inspired radioprotectors. PLoS One 4, e7229
7. Cabrera-Valladares, N., Martinez, A., Pinero, S., Lagunas-Munoz, V. H., Tinoco, R., de Anda, R., Vazquez-Duhalt, R., Bolivar, F., and Gosset, G. (2006) Expression of the melA gene from Rhizobium etli CFN42 in *Escherichia coli* and characterization of the encoded tyrosinase. Enzyme Microb Tech 38, 772-779
8. Gustaysson, M., Hornstrom, D., Lundh, S., Belotserkovsky, J., and Larsson, G. (2016) Biocatalysis on the surface of *Escherichia coli*: melanin pigmentation of the cell exterior. Sci Rep-Uk 6.
9. Wang, Z., Lin, B., Hervey, W. J. t., and Vora, G. J. (2013) Draft Genome Sequence of the Fast-Growing Marine Bacterium *Vibrio natriegens* Strain ATCC 14048. Genome Announc. 1(e): e00589-13.
10. Wang, Y. L., Aisen, P., and Casadevall, A. (1996) Melanin, melanin "ghosts," and melanin composition in *Cryptococcus neoformans*. Infect Immun 64, 2420-2424.
11. US Army Center for Health Promotion and Preventative Medicine Technical Guide 230: Chemical Exposure Guidelines for Deployed Military Personnel. (2004).
12. Norton, F. J., Schenectady, N.Y. "Waterproofing treatment of materials" U.S. Pat. No. 2,386,259. October 1945.
13. White, B. J., Melde, B. J. "Microwave initiation for deposition of porous organosilicate materials on fabrics" U.S. Pat. No. 9,689,111. October 2017.
14. Meredith, P., Subianto, S., Will, G. "Process for the Production Of Thin Films Of Melanin And Melanin-like Molecules By Electrosynthesis" WO/2005/026216 March 2005.
15. Kawai, R., Aoki, Y, Aoki, E., Takakuwa, K., Namiki, M. "Process for producing melanin, melanin produced by the process, functional film containing the melanin, and process for producing the same" US 2009/0317616 A1 Dec. 2009.

16. Gallas, J. M. "Medium incorporating melanin as an absorbing pigment against electromagnetic radiation" U.S. Pat. No. 5,112,883. 1992.
17. "Deposition of porous sorbents on fabric supports" B. J. Johnson, B. J. Melde, M. H. Moore, J. R. Taft, J Vis Exp. 2018 Jun. 12; (136).
18. "Permeation Tests on Polypropylene Fiber Materials" B. J. White, M. H. Moore, B. J. Melde. 2018 NRL Memorandum Report #NRL/MR/6930-18-9771.
19. "Functionalized organosilicate sorbents for air purification" B. J. White, B. J. Melde, M. H. Moore, G. W. Peterson. 2013 NRL Formal Report #NRL/FR/6920-13-10,251.
20. "Synthesis of hydrophobic and oleophobic nylon-cotton fabric through microwave catalyzed silane attachment," J. R. Owens, R. A. Hayn, S. A. Boyer, R. S. McDonald. 2008, AFRL Report #AFRL-RX-TY-TP-20084619.
21. "Preparation of highly hydrophobic and oleophobic textile surfaces using microwave-promoted silane coupling," R. A. Hayn; J. R. Owens; S. A. Boyer; R. S. McDonald; H. J. Lee. 2011, Journal of Materials Science 46, 2503-2509
21. "An Update on Nanomaterials-Based Textiles for Protection and Decontamination," S. Sundarrajan, A. R. Chandrasekaran, S. Ramakrishna 2010, J. Am. Ceram. Soc. 93, 3955-3975.
22. Meredith, P., and Sarna, T. (2006) The physical and chemical properties of eumelanin. Pigment Cell Res 19, 572-594
23. Micillo, R., Panzella, L., Koike, K., Monfrecola, G., Napolitano, A., and d'Ischia, M. (2016) "Fifty Shades" of Black and Red or How Carboxyl Groups Fine Tune Eumelanin and Pheomelanin Properties. Int J Mol Sci 17
24. Eisenman, H. C., and Casadevall, A. (2012) Synthesis and assembly of fungal melanin. Appl Microbiol Biotechnol 93, 931-940
25. Kim, Y J., Khetan, A., Wu, W, Chun, S. E., Viswanathan, V., Whitacre, J. F., and Bettinger, C. J. (2016) Evidence of Porphyrin-Like Structures in Natural Melanin Pigments Using Electrochemical Fingerprinting. Adv Mater 28, 3173-3180
26. Farthmann, B., Schmitz, S., Krasagakis, K., Orfanos, C. E. Photoprotection by total melanin content and pigment phenotype (eumelanin, pheomelanin) in human melanoma cell lines. *Skin Cancer and UV Radiation*. Springer-Verlag, Berlin. p 181-185 (1997).
27. Y. T. Gebreegzi; G. D. Foster; S. U. Khan, "Simulltaneous Determination of Carbaryl, Malathion, Fenitrothion, and Diazinon Residues in Sesame Seeds (Seasmum indicum L)" *J. Agric. Food Chem.* 48, 5165-5168 (2000)
28. "Adsorption of organophosphates from solution by porous organosilicates: Capillary phase-separation" B. J. Johnson, A. P. Malanoski, I. A. Leska, B. J. Melde, J. R. Taft, M. A. Dinderman, J. R. Deschamps, *Microporous Mesoporous Materials,* 195, 154-60 (2014).

What is claimed is:

1. A material comprising fabric in a state of being modified via microwave treatment, and melanin chemically bonded to the fabric.
2. The material of claim 1, wherein the modification comprises microwave initiation with 3-aminopropyltriethoxysilane and the chemical bonding comprises bonding with 1-ethyl-3-(3-dimethylaminopropyl)carbodiimide.
3. The material of claim 1, wherein the melanin is pheomelanin.
4. The material of claim 1, wherein the melanin is eumelanin.
5. The material of claim 1, wherein the melanin has been obtained from *Vibrio natriegens*.
6. A method of bonding melanin to fabric, the method comprising:
   chemically treating a fabric to make it amenable to melanin binding;
   irradiating the treated fabric with microwave radiation; and
   bonding the melanin to the irradiated fabric.
7. The method of claim 6, wherein the chemical treatment comprises treatment with 3-aminopropyltriethoxysilane and the bonding comprises bonding with 1-ethyl-3-(3-dimethylaminopropyl)carbodiimide.
8. The method of claim 6, wherein the melanin is pheomelanin.
9. The method of claim 6, wherein the melanin is eumelanin.
10. The method of claim 6, wherein the melanin has been obtained from *Vibrio natriegens*.

* * * * *